(12) United States Patent
Ekwuribe (10) Patent No.: US 7,022,869 B2
(45) Date of Patent: Apr. 4, 2006

(54) METHODS OF ASYMMETRICALLY SYNTHESIZING ENANTIOMERS OF CASODEX, ITS DERIVATIVES AND INTERMEDIATES THEREOF

(75) Inventor: Nnochiri Nkem Ekwuribe, Cary, NC (US)

(73) Assignee: Nobex Corporation, Durham, NC (US)

( * ) Notice: Subject to any disclaimer, the term of this patent is extended or adjusted under 35 U.S.C. 154(b) by 214 days.

(21) Appl. No.: 10/444,343

(22) Filed: May 23, 2003

(65) Prior Publication Data

US 2004/0030130 A1    Feb. 12, 2004

Related U.S. Application Data

(62) Division of application No. 09/691,621, filed on Oct. 18, 2000, now Pat. No. 6,583,306.

(60) Provisional application No. 60/160,412, filed on Oct. 19, 1999.

(51) Int. Cl.
C07C 255/50    (2006.01)
(52) U.S. Cl. ...................... 558/354; 558/393
(58) Field of Classification Search ................ 558/354, 558/393
See application file for complete search history.

(56) References Cited

U.S. PATENT DOCUMENTS

| | | | |
|---|---|---|---|
| 4,636,505 A | 1/1987 | Tucker | 514/256 |
| 4,880,839 A | 11/1989 | Tucker | 514/613 |
| 5,985,868 A | 11/1999 | Gray | 514/220 |
| 6,019,957 A | 2/2000 | Miller et al. | 424/1.65 |

FOREIGN PATENT DOCUMENTS

WO    WO98/55153    12/1998

OTHER PUBLICATIONS

Barton et al.; "A Practical Alternative to The Hunsdiecker Reaction" *Tetrahedron Letters*, 24:45 4979-4982 (1983).
Beckwith et al.; "Some Diastereoselective Radical Reactions of Substituted 1,3-Dioxolan-4-ones" *Tetrahedron* 49:36 7871-7882 (1993).
Eggerer et al; "Synthese von Citramalyl-coenzym A und Nachweis seiner enzymatischen Adolspaltung" *Biochemische Zeitschrift* 342 40-53 (1965).
Farines et al.; "Étude de dioxolanones-4: synthèse et propriétés physiques" *Bulletin De La Société Chimique De France*, No. 1 332-340 (1970).
Hof et al.; "Synthesis and Lipase-Catalyzed Resolution of 5-(Hydroxymethyl)-1,3-dioxolan-4-ones: Masked Glycerol Analogs as Potential Building Blocks for Pharmaceuticals" *J. Org. Chem.* 61 3423-3427 (1996).
Tucker et al., "Resolution of the Nonsteroidal Antiandrogen 4'-Cyano-3-[(4-fluorophenyl)sulfonyl]-2-hydroxy-2-methyl-3'-(trifluoromethyl)-propionanilide and the Determination of the Absolute Configuration of the Active Enantiomer," *J. Med. Chem.* 31:4 885-887 (1988).
Tucker et al.; "Nonsteroidal Antiandrogens. Synthesis and Structure-Activity Relationships of 3-Substituted Derivatives of 2-Hydroxypropionanilides" *J. Med. Chem.* 31 954-959 (1988).
Zeuner et al.; "Synthese und Polymerisation von 2-Aryl-5-methylen-1,3-dioxolan-4-onen und Arylbis(5-methylen-1,3-dioxolan-2-yl-4-on)en" *J. prakt. Chem.* 337 478-485 (1995).

*Primary Examiner*—Thomas C. McKenzie
(74) *Attorney, Agent, or Firm*—William A. Barrett; Moore & Van Allen PLLC (57) ABSTRACT

Methods of synthesizing pure enantiomers of acylanalides such as Casodex® (bicalutamide) and its derivatives utilizing a compound having a ring structure that, when opened, provides a substituent having the structure of Formula I:

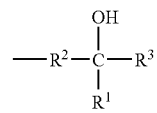

Formula I wherein
  $R^1$ is alkyl or haloalkyl having up to 4 carbons;
  $R^2$ is alkyl having up to 6 carbon atoms; and
  $R^3$ is $CH_2OR^4$ where $R^4$ is hydrogen or benzyl, $C(O)CH_3$, or $C(O)OR^5$ where $R^5$ is hydrogen or alkyl;
are disclosed.

5 Claims, 3 Drawing Sheets

METHODS OF ASYMMETRICALLY SYNTHESIZING ENANTIOMERS OF CASODEX, ITS DERIVATIVES AND INTERMEDIATES THEREOF

RELATED APPLICATIONS

This application is a divisional application of, and claims priority to, U.S. patent application Ser. No. 09/691,621, filed Oct. 18, 2000, now U.S. Pat. No. 6,583,306, issued Jun. 24, 2003, which claims priority to U.S. Provisional Application No. 60/160,412, filed Oct. 19, 1999, the disclosures of each of which are incorporated herein by reference in their entireties.

FIELD OF THE INVENTION

The present invention relates to methods of synthesizing organic compounds, and more particularly to methods of asymmetrically synthesizing optically active pharmaceutical compounds and their intermediates.

BACKGROUND OF THE INVENTION

Androgen deprivation is a common treatment for persons with prostate cancer. Various non-steroidal antiandrogens are known for use in the treatment of prostate cancer. For example, bicalutamide, which may be among the most commonly used non-steroidal antiandrogens in the world, is typically used in the treatment of prostate cancer. Bicalutamide is commercially available as Casodex® (bicalutamide) from Zeneca Pharmaceuticals.

The chemical name of bicalutamide is N-[4-cyano-3-(trifluoromethyl)phenyl]-3-[(4-fluorophenyl)sulfonyl]-2-hydroxy-2-methyl-propanamide,(+−). The structural formula of bicalutamide is:

The β-carbon atom in the propanamide is a chiral carbon. As a result, bicalutamide is an optically active compound.

Optically active compounds have the ability to rotate the plane of polarized light. In describing an optically active compound, the prefixes D and L or R and S are used to denote the absolute configuration of the molecule about its chiral center(s). The prefixes d and l or (+) and (−) are used to denote the optical rotation of the compound (i.e., the direction in which a plane of polarized light is rotated by the optically active compound). The l or (−) prefix indicates that the compound is levorotatory (i.e., rotates the plane of polarized light to the left or counterclockwise) while the d or (+) prefix means that the compound is dextrarotatory (i.e., rotates the plane of polarized light to the right or clockwise). The sign of optical rotation, (−) and (+), is not related to the absolute configuration of the molecule, R and S.

Optically active compounds, such as bicalutamide, exist as a pair of stereoisomers that are identical with the notable exception that they are non-superimposable mirror images of one another. A specific stereoisomer, such as the R isomer, may be referred to as an enantiomer. A mixture of R and S enantiomers may be referred to as a racemic mixture.

Bicalutamide, is presently commercially available as a racemic mixture. The racemic mixture of bicalutamide may be synthesized by various methods including, for example, the methods described in U.S. Pat. No. 4,636,505 to Tucker. Tucker further describes various derivatives and analogs of bicalutamide having antiandrogenic properties. Tucker, however, does not disclose or suggest methods for asymmetrically synthesizing enantiomers of Casodex® (bicalutamide) and/or its intermediates.

U.S. Pat. No. 5,985,868 to Gray proposes synthesizing racemic mixtures of Casodex® (bicalutamide) using methods as described in U.S. Pat. No. 4,636,505 to Tucker, and obtaining the (−) isomer of Casodex® (bicalutamide) by resolution of the enantiomers of Casodex® (bicalutamide) or of intermediates thereto using fractional crystallization or chromatography of diastereomeric esters of chiral acids. Gray notes that other standard methods of resolution such as simple crystallization and chromatographic resolution can also be used. Gray does not disclose or suggest methods of asymmetrically synthesizing enantiomers of Casodex® (bicalutamide) and/or its derivatives and/or intermediates.

In Howard Tucker et al., *Resolution of the Nonsteroidal Antiandrogen 4'-Cyano-3-[(4-fluorophenyl)sulfonyl]-2-hydroxy-2-methyl-3'-(trifluoromethyl)- propioanilide and the Determination of the Absolute Configuration of the Active Enantiomer*, 31 J. MED. CHEM. 885–887 (1988), the authors propose an asymmetric synthesis of (S)-Casodex® (bicalutamide) using the N-methacrylamide of (S)-proline as a starting material. The proposed reaction scheme is as follows:

-continued

The authors state that this approach is not suitable for the general synthesis of the active enantiomers of analogous anti-androgens, which would require the inaccessible and expensive (R)-proline as a starting material.

U.S. Pat. No. 6,019,957 to Miller et al. proposes an asymmetric synthesis of (R)-Casodex® (bicalutamide) using (R)-proline as a starting material. The proposed reaction scheme is as follows:

As noted above, (R)-proline is an inaccessible and expensive starting material. It would be desirable to provide more cost effective methods for asymmetrically synthesizing enantiomers of Casodex® (bicalutamide) and/or its derivatives and/or intermediates that do not rely on (R)-proline as a starting material.

SUMMARY OF THE INVENTION

Embodiments of the present invention provide methods for asymmetrically synthesizing enantiomers of Casodex® (bicalutamide) and/or its intermediates. Asymmetric synthesis methods according to embodiments of the present invention are more cost effective than conventional methods. For example, asymmetric synthesis methods according to embodiments of the present invention react 4-fluorobenzenethiol with the bromolactone of Formula 1 or 2 above. By reacting the 4-fluorobenzenethiol with the bromolactone prior to hydrolyzing the bromolactone instead of hydrolyzing the bromolactone and then reacting the 4-fluorobenzenethiol with the resulting acid as proposed above, improved separation of the reaction products and thus higher yields may be provided. Furthermore, asymmetric synthesis methods according to embodiments of the present invention produce (R)-Casodex® (bicalutamide) and/or its intermediates using (S)-citramalic acid (2-hydroxy-2-methylbutanedioic acid) as a starting material, which may be more cost effective than the conventional scheme, which uses the inaccessible and expensive (R)-proline as a starting material.

According to embodiments of the present invention, methods of asymmetrically synthesizing an enantiomer of an acylanalide such as Casodex® (bicalutamide) or its derivatives are provided. The methods include contacting a compound having a ring structure that, when opened, provides a substituent having the structure of Formula I:

Formula I wherein
$R^1$ is alkyl or haloalkyl having up to 4 carbons;
$R^2$ is alkyl having up to 6 carbon atoms; and
$R^3$ is $CH_2OR^4$ where $R^4$ is hydrogen or benzyl, $C(O)CH_3$, or $C(O)OR^5$ where $R^5$ is hydrogen or alkyl;

with a compound having a structure of Formula II:

Formula II wherein
$R^6$ is a direct link or alkyl having up to 6 carbon atoms;
$R^7$ is alkyl, alkenyl, hydroxyalkyl or cycloalkyl each of up to 6 carbons; or $R^7$ is phenyl which bears one, two or three substituents independently selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl; or $R^7$ is naphthyl; or $R^7$ is a 5- or 6-membered saturated or unsaturated heterocyclic which contains one, two or three heteroatoms selected from oxygen, nitrogen and sulfur, which heterocyclic may be a single ring or may be fused to a benzo-ring, and which heterocyclic is unsubstituted or bears one or two halogen, cyano or amino, or alkyl, alkoxy, alkylthio, alkylsulphinyl or alkylsulphonyl each of up to 4 carbon atoms, or oxy or hydroxy substituents, or which if sufficiently saturated may bear one or two oxo substituents; and $X^1$ is oxygen, sulfur, sulphinyl (—SO—), sulphonyl (—$SO_2$—), imino (—NH—) or alkylimino (—$NR^8$—) where $R^8$ is alkyl having up to 6 carbon atoms;

under conditions sufficient to provide a compound having the structure of Formula III:

Formula III wherein $X^2$ is oxygen, sulfur, sulphinyl (—SO—), sulphonyl (—$SO_2$—), imino (—NH—), oxidized imino alkylimino (—$NR^8$—) where $R^8$ is alkyl having up to 6 carbon atoms, or oxidized alkylimino. The method further includes treating the compound of Formula III under conditions sufficient to provide a pure enantiomer of Casodex® (bicalutamide) or a pure enantiomer of a Casodex® (bicalutamide) derivative. In preferred embodiments, $R^1$ is methyl, $R^2$ is methylene, $R^6$ is a direct link, $R^7$ is 4-fluorophenyl, $X^1$ is sulfur, the compound of Formula II is 4-fluorobenzenethiol, and $X^2$ is sulphonyl.

In other embodiments according to the present invention, the compound having a ring structure is a compound of Formula IV:

Formula IV wherein
  $R^9$ is hydrogen, or straight, branched or cyclic alkyl;
  $R^{10}$ is straight or branched alkyl, aryl, or $R^{11}X_3^4$, where $R^{11}$ is alkyl and $X^4$ is alkyl, halogen or aryl; and
  $X^3$ is a leaving group.

The compound of Formula IV is contacted with the compound of Formula II under conditions sufficient to provide a compound having the structure of Formula V:

Formula V

In preferred embodiments, $R^1$ is methyl and $R^2$ is methylene. In particularly preferred embodiments, citramalic acid is used as a starting material to provide a compound having the structure of Formula IV. The citramalic acid may be either the (R) or the (S) enantiomer; however, it is preferable to use the (S)-enantiomer of citramalic acid because it may be more readily available and thus, unlike (R)-proline, may be a relatively inexpensive starting material in the synthesis of arylanilides such as Casodex® (bicalutamide) and/or its derivatives. Furthermore, the more active form of Casodex® (bicalutamide) ((R)-Casodex® (bicalutamide)) can be synthesized according to methods of the present invention using (S)-citramalic acid.

In still other embodiments according to the present invention, the compound having a ring structure is a compound of Formula VIII:

Formula VIII wherein $X^5$ is a leaving group. The compound of Formula VIII is contacted with the compound of Formula II under conditions sufficient to provide a compound having the structure of Formula IX:

Formula IX

In yet other embodiments of the present invention, the compound having a ring structure is a compound of Formula XI:

Formula XI

The compound of Formula XI is contacted with the compound of Formula II under conditions sufficient to provide a compound having the structure of Formula XII:

Formula XII

In preferred embodiments, the compound of Formula III is treated with a compound having the structure of Formula XIII:

Formula XIII wherein
  $R^{13}$ is cyano, carbamoyl, nitro, fluoro, chloro, bromo, iodo, or hydrogen, or alkyl, alkoxy, alkanoyl, alkylthio, alkylsulphinyl, alkylsulphonyl, perfluoroalkyl, perfluoroalkylthio, perfluoroalkylsulphinyl or perfluoroalkylsulphonyl each having up to 4 carbon atoms, or phenylthio, phenylsulphinyl or phenylsulphonyl;
  $R^{14}$ is cyano, cabamoyl, nitro, fluoro, chloro, bromo or iodo, or alkanoyl, alkylthio, alkylsulphinyl, alkylsulphonyl, perfluoroalkyl, perfluoroalkylthio, perfluoroalkylsulphinyl or perfluoroalkylsulphonyl each of having up to 4 carbon atoms; or phenylthio, phenylsulphinyl or phenylsulphonyl; and
  $R^{15}$ is hydrogen or halogen;

under conditions sufficient to provide a compound of Formula XIV:

Formula XIV wherein $X^2$ is oxygen, sulfur, sulphinyl (—SO—), sulphonyl (—$SO_2$—), imino (—NH—), oxidized imino alkylimino (—$NR^8$—) where $R^8$ is alkyl having up to 6 carbon atoms, or oxidized alkylimino. In preferred embodiments, the compound of Formula XIII is 4-amino-2-trifluoromethylbenzonitrile, and the compound of Formula XIV is Casodex® (bicalutamide).

Asymmetric synthesis methods according to the present invention may provide pure enantiomers of Casodex® (bicalutamide) and/or its intermediates in a more cost effective manner than conventional methods. For example, as noted above, conventional methods that attempt to provide the more active (R)-enantiomer of Casodex® (bicalutamide) do so either by synthesizing ester derivatives of the racemic mixture and then separating the (R) enantiomer from the (S) enantiomer to produce a Casodex® (bicalutamide) mixture having a higher concentration of (R) enantiomer than (S) enantiomer or by asymmetrically synthesizing the (R)-enantiomer using the inaccessible and expensive (R)-proline as a starting material. By asymmetrically synthesizing the (R) enantiomer of Casodex® (bicalutamide) rather than synthesizing and then separating a racemic mixture, methods according to embodiments of the present invention eliminate the economic waste associated with discarding the (S) enantiomer. Furthermore, according to embodiments of the present invention, (R)-Casodex® (bicalutamide) is asymmetrically synthesized using the readily available (S)-citramalic acid as a starting material rather than the inaccessible and expensive (R)-proline.

DETAILED DESCRIPTION OF PREFERRED EMBODIMENTS

The invention will now be described with respect to preferred embodiments described herein. It should be appreciated however that these embodiments are for the purpose of illustrating the invention, and are not to be construed as limiting the scope of the invention as defined by the claims. As the substituents $R^1$–$R^{15}$, $X^1$–$X^5$ have been defined above, they will not be further defined herein other than to describe preferred substituents for the preferred embodiments.

Embodiments of the present invention provide methods of asymmetrically synthesizing an enantiomer of an acylanilide. Particularly preferred methods provide synthesis routes for Casodex® (bicalutamide) and its derivatives that are more cost effective than conventional preparation techniques.

In a first embodiment, methods of asymmetrically synthesizing an enantiomer of acylanilide comprises contacting a compound having a ring structure that, when opened, provides a substituent having the structure of Formula I:

Formula I with a compound having a structure of Formula II:

Formula II under conditions sufficient to provide a compound having the structure of Formula III:

Formula III and, synthesizing the compound of Formula III under conditions sufficient to provide a pure enantiomer of an acylanilide. The pure enantiomer of the acylanilide is preferably a pure enantiomer of Casodex® (bicalutamide) or a derivative thereof. More preferably, the pure enantiomer of the acylanilide is (R)-Casodex® (bicalutamide) or a derivative thereof.

Preferably, $R^1$ and $R^2$ are each lower alkyl having up to 6 carbons. More preferably, $R^1$ is methyl and $R^2$ is methylene. $R^3$ is preferably $CH_2)H$ or $C(O)OH$. Preferably $R^6$ is a direct link (i.e., one or more bonds between $X^1$ and $R^7$). $R^7$ is preferably phenyl which bears one, two or three substituents independently selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl. More preferably, $R^7$ is phenyl which bears one, two or three substituents independently selected from hydrogen and halogen. Most preferably, $R^7$ is 4-fluorophenyl. Preferably, $X^1$ is sulfur, sulphinyl, sulphonyl or imino. $X^1$ is more preferably sulfur, sulphinyl, or sulphonyl and is most preferably sulfur. $X^2$ is preferably sulphonyl.

Figure 1:
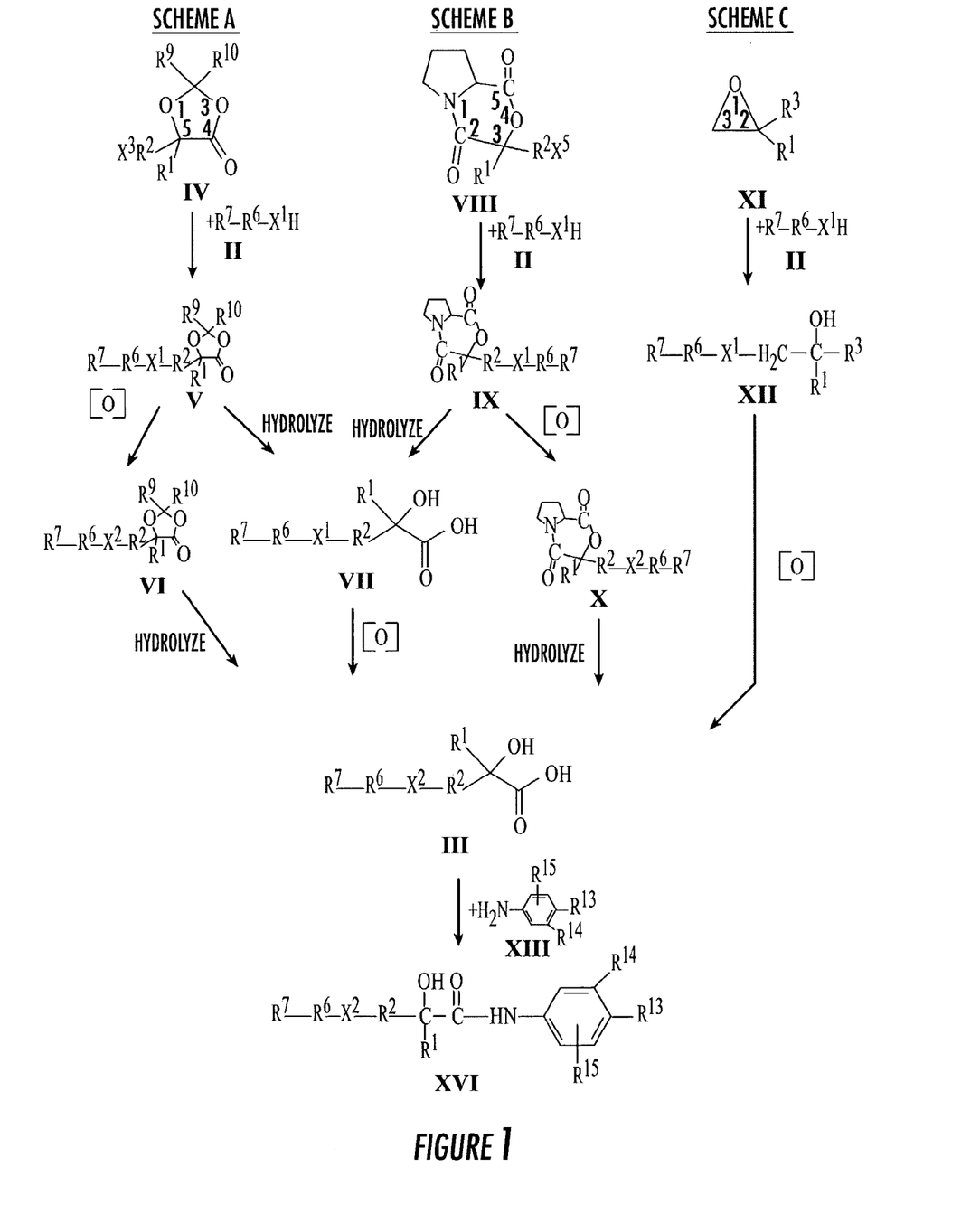
FIG. 1 illustrates a reaction scheme for synthesizing acylanilides such as Casodex® (bicalutamide) that includes attaching the compound of Formula II to compounds having ring structures according to the present invention.

Referring to FIG. 1, embodiments of preferred compounds having ring structures that, when opened, provide substituents having the structure of Formula I:

Formula I will now be described. Referring first to Scheme A, the compound having a ring structure is a compound of Formula IV:

Formula IV

The compound of Formula IV contacts the compound of Formula II under conditions sufficient to provide a compound having the structure of Formula V:

Formula V

As illustrated in FIG. 1, Scheme A, the compound of Formula V may follow one of two separate synthesis routes to provide the compound of Formula III. The compound of Formula V may be oxidized to convert $X^1$ to $X^2$ providing the compound of Formula VI, which may then be hydrolyzed to open the lactone (heterocyclic ring) of Formula VI, providing the compound of Formula III. Alternatively, the compound of Formula V may be hydrolyzed to deprotect the hydroxy acid and provide the compound of Formula VII, which may then be oxidized to convert $X^1$ to $X^2$, providing the compound of Formula III. While the synthesis routes shown in FIG. 1, Scheme A show an oxidation step, it is to be understood that an oxidation step may not be required. For example, an oxidation step may not be required when $X^1$ is sulphonyl, when the oxidation step occurs later in the process (e.g., after the amidation step), or when the acylanilide derivative is not fully oxidized. As will be understood by those skilled in the art, various means may be used to hydrolyze the lactone, including, but not limited to, contacting the lactone of Formula V with an aqueous acid or aqueous base solution. The lactone of Formula V is preferably hydrolyzed using HCl. Those in the art will also understand that a variety of methods and agents may be used to oxidize the compound of Formula V to obtain the compound of Formula III.

Preferably, $R^9$ and $R^{10}$ are selected to allow for hydrolysis of the lactone of Formula IV. $R^9$ is preferably hydrogen, or straight, branched or cyclic lower alkyl. More preferably, $R^9$ is hydrogen. $R^{10}$ is preferably aryl or $R^{11}X_3^4$ where $R^{11}$ is lower alkyl and $X^4$ is lower alkyl, halogen, or aryl. More preferably, $R^{10}$ is benzyl or $R^{11}X_3^4$ where $R^{11}$ is methyl and $X^4$ is methyl, Cl, Br, or phenyl. $X^3$ is a leaving group, as will be understood by those skilled in the art. $X^3$ is preferably halogen, and is more preferably bromine.

Figure 2:
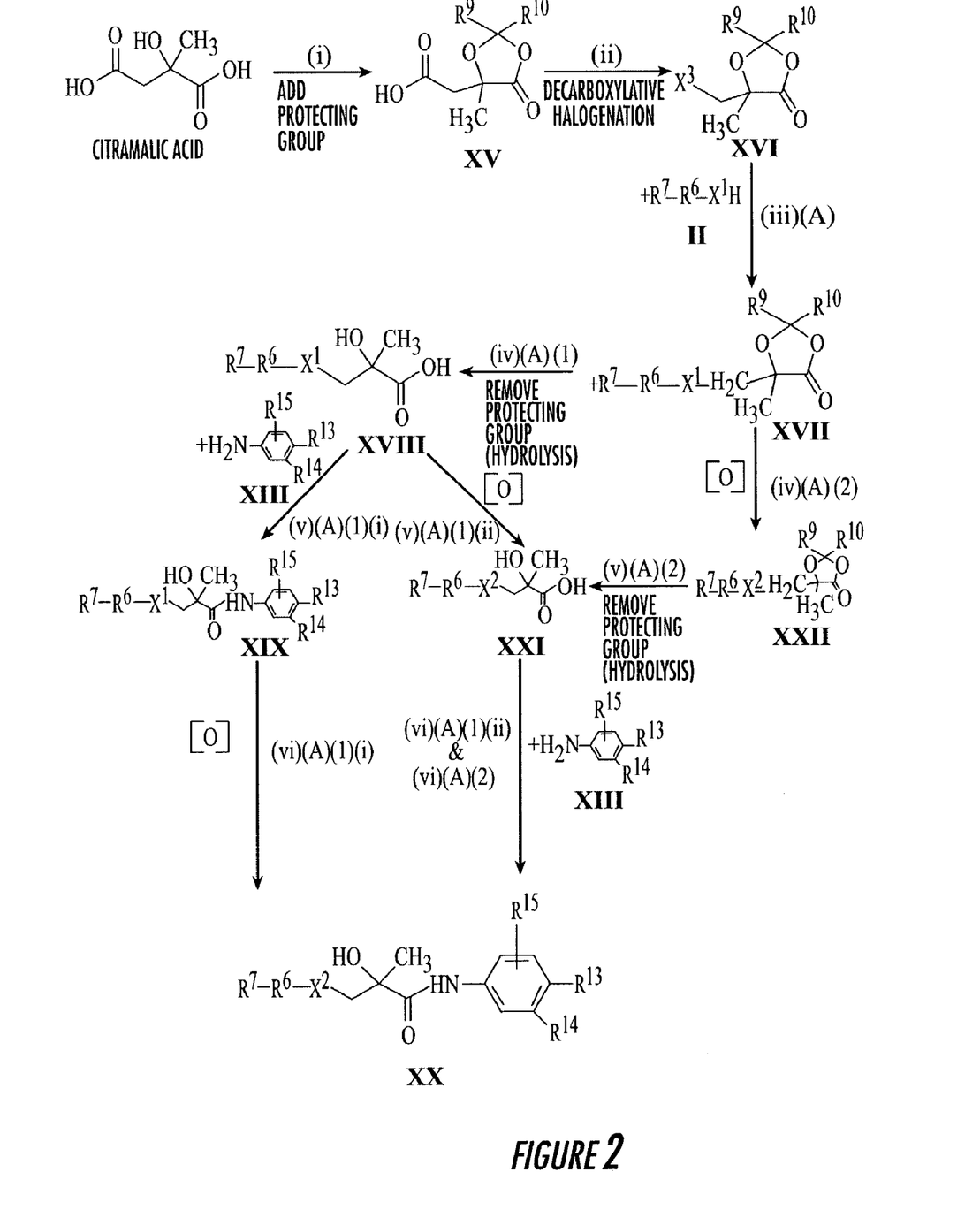
FIG. 2 illustrates three routes for synthesizing acylanilides such as Casodex® (bicalutamide) using citramalic acid as a starting material and attaching the compound of Formula II to the heterocyclic ring structure prior to hydrolyzing the heterocycle according to the present invention.
Figure 3:
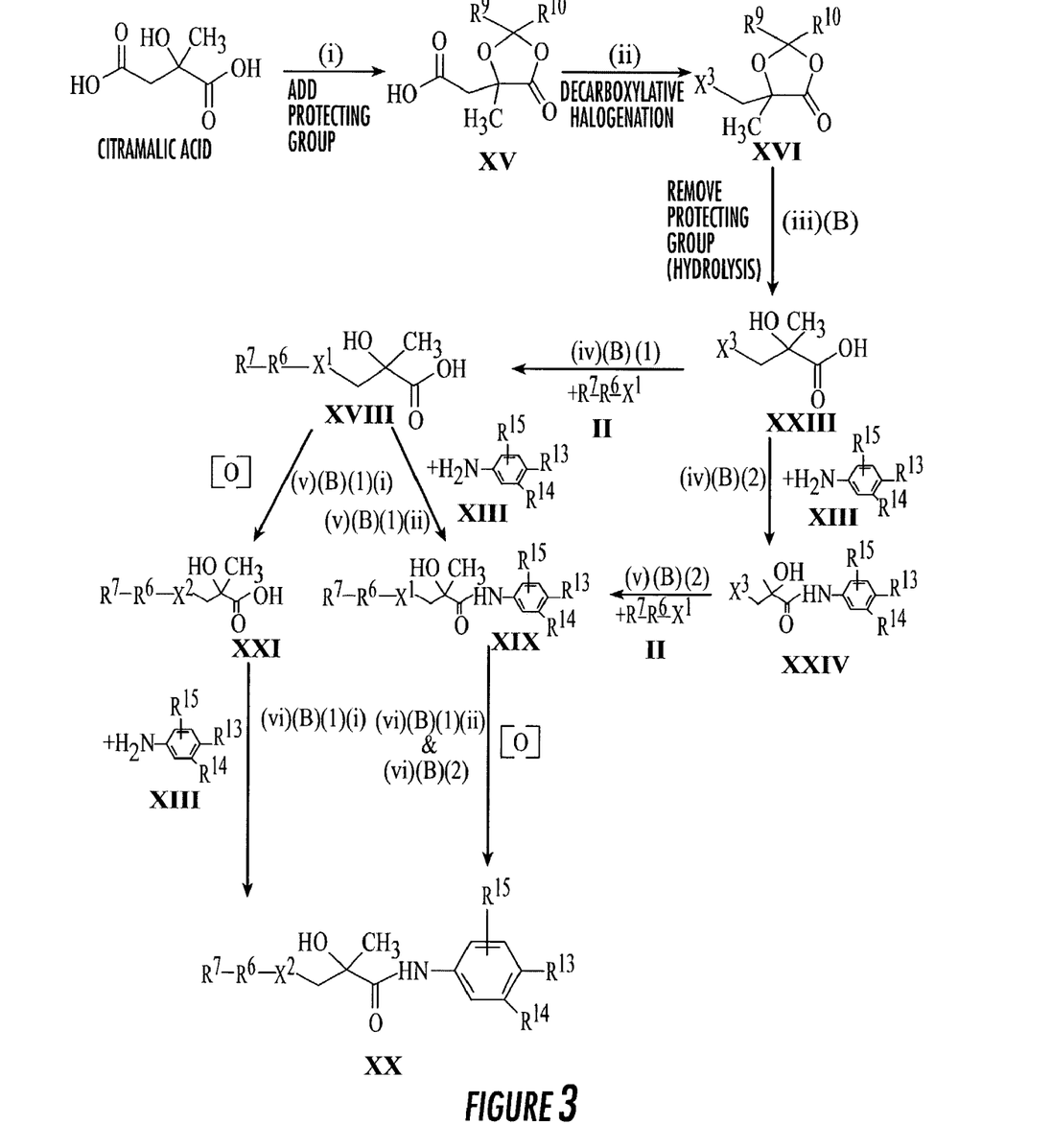
FIG. 3 illustrates three routes for synthesizing acylanilides such as Casodex® (bicalutamide) using citramalic acid as a starting material and hydrolyzing the heterocycle before reacting the citramalic acid derivative with the compound of Formula II according to the present invention.

In a most preferred embodiment, the compound of Formula IV is synthesized from citramalic acid, as illustrated in FIGS. 2 and 3, which will now be described. The following synthesis routes may be employed using (R)-citramalic acid, (S)-citramalic acid, or a racemic mixture thereof as the starting material. Citramalic acid is commercially available from Fluka, a business unit of Sigma-Aldrich Corporation of St. Louis, Mo. For the synthesis of the acylanalide Casodex® (bicalutamide) and its derivatives, it is preferable to use (S)-citramalic acid as the starting material. (S)-citramalic acid may be used as a starting material in methods of the present invention to provide (R)-Casodex® (bicalutamide). (R)-Casodex® (bicalutamide) is believed to be the most active Casodex® (bicalutamide) enantiomer for the treatment of prostate cancer, as well as other androgen related diseases. In sharp contrast to the (R)-proline starting material, which is inaccessible and expensive, (S)-citramalic acid is readily available. Thus, the synthesis methods of the present invention that utilize (S)-citramalic acid as a starting material may be more cost effective than conventional methods that rely on (R)-proline.

The various synthesis routes illustrated in FIGS. 2 and 3 are denoted by the designations next to the reaction arrows. The primary designator (the initial small roman numeral) designates the step number, while the secondary designator(s) (the capital letter, the arabic numeral, and the second small roman numeral) designate the particular route. Synthesis routes having steps that have all of the secondary designators of an earlier step in common have that step in common. For example, in FIG. 2, the steps (vi)(A)(1)(i) and (v)(A)(1)(ii) have all of the secondary designators of step (iv)(A)(1) in common; therefore, step (iv)(A)(1) is a step in both the (A)(1)(i) synthesis route as well as the (A)(1)(ii) synthesis route.

Turning first to FIG. 2, in step (i) a protecting group is added to the citramalic acid to provide the compound of Formula XV. The protecting group is used to protect the hydroxy acid from the decarboxylation step (ii) by forming the dioxolanone of Formula XV. The protecting group may also add molecular weight to the citramalic acid molecule. This larger citramalic acid derivative may be more easily separated after formation of the sulfide as compared to derivatives from which the protecting group is removed prior to formation of the sulfide (e.g., FIG. 3, steps (iii)(B) and (iv)(B)(1)). The protecting group is preferably added by aldol condensation reaction, and more preferably is added by the aldol condensation reaction of bromal and citramalic acid in the presence of sulfuric acid.

In step (ii), the compound of Formula XV undergoes decarboxylative halogenation to provide the compound of Formula XVI. To avoid the heavy metals associated with the Hunsdiecker reaction, it is preferable to use the decarboxylative bromination method proposed by Barton et al. in 24 TETRAHEDRON LETT. 4979–4982 (1983), which is incorporated herein by reference in its entirety. An example of this bromination method is provided in Example 2, described hereinbelow. While FIGS. 2 and 3 show a step (ii) that is a decarboxylative halogenation step, it will be understood by those skilled in the art that various decarboxylation steps may be used, such as other decarboxylation steps that replace the carboxylic acid group with a non-halogen leaving group.

In step (iii)(A), the compound of Formula II is added to the compound of Formula XVI to provide the compound of Formula XVII. The compound of Formula II is preferably added by a substitution reaction, as will be understood by those skilled in the art. An example of this substitution reaction is provide in Example 3, described hereinbelow.

Referring now to synthesis route (A)(2), the compound of Formula XVII is oxidized in step (iv)(A)(2) to provide the compound of Formula XXII. The protecting group is then removed from the compound of Formula XXII in step (v)(A)(2), preferably by hydrolysis, to provide the compound of Formula XXI. In step (vi)(A)(2), the compound of Formula XIII is then added to the compound of Formula XXI to provide the acylanilide of Formula XX. The amidation may be performed by various methods as will be understood by those skilled in the art. The amidation is preferably accomplished via in situ generation of the acid chloride. Thionly chloride is the preferred for this procedure.

Synthesis routes (A)(1)(i) and (A)(1(ii) utilize processes similar to those described for synthesis route (A)(2), and will not be further described. Referring to FIG. 3, the synthesis routes (B)(1)(i) and (B)(2) utilize processes similar to those described for synthesis route (A)(2), and will not be further described. Synthesis route (B)(1)(ii) utilizes processes similar to those employed in the other synthesis routes of FIGS. 2 and 3. Synthesis route (B)(1)(ii) is described in some detail in Examples 1–5 hereinbelow. Thus, citramalic acid may be used as a starting material to form the compound of Formula IV:

Formula IV which has a ring structure that, when opened, provides a substituent having the structure of Formula I:

Formula I

Returning to FIG. 1, Scheme B illustrates other methods according to embodiments of the present invention where the compound having a ring structure that, when opened, provides a substituent having the structure of Formula I is a compound having the structure of Formula VIII:

Formula VIII

The compound of Formula VIII may be made, for example, according to the synthesis routes described, for example, in U.S. Pat. No. 6,019,957 to Miller et al. and Howard Tucker et al., *Resolution of the Nonsteroidal Antiandrogen 4'-Cyano-3-[(4-fluorophenyl)sulfonyl]-2- hydroxy-2-methyl-3'-(trifluoromethyl)-propioanilide and the Determination of the Absolute Configuration of the Active Enantiomer*, 31 J. MED. CHEM. 885–887 (1988), the disclosures of which are incorporated herein by reference in their entireties. As noted above, $X^5$ is a leaving group. $X^5$ is preferably halogen and is more preferably bromine.

The compound of Formula VIII contacts the compound of Formula II under conditions sufficient to provide a compound having the structure of Formula IX:

Formula IX

The compound of Formula II is preferably added to the compound of Formula VIII via a substitution reaction, as will be understood by those skilled in the art. For example, a substitution reaction similar to the one described below in Example 3 may be used.

As illustrated in FIG. 1, Scheme B, the compound of Formula IX may follow one of two separate synthesis routes to provide the compound of Formula III. The compound of Formula IX may be hydrolyzed to deprotect the hydroxy acid and provide the compound of Formula VII, which may then be oxidized to convert $X^1$ to $X^2$, providing the compound of Formula III. Alternatively, the compound of Formula IX may be oxidized to convert $X^1$ to $X^2$ providing the compound of Formula X, which may then be hydrolyzed to open the 6-membered heterocyclic ring of Formula X, providing the compound of Formula III. While the synthesis routes shown in FIG. 1, Scheme B show an oxidation step, it is to be understood that an oxidation step may not be required and/or desired. For example, an oxidation step may not be required and/or desired when $X^1$ is sulphonyl, when the oxidation step occurs later in the process (e.g., after the amidation step), or when the acylanilide derivative is not fully oxidized. As will be understood by those skilled in the art, various means may be used to hydrolyze the 6-membered heterocyclic ring, including, but not limited to, contacting the heterocyclic ring of Formula IX with an aqueous acid or aqueous base solution. Preferably, the compound of Formula IX is hydrolyzed using HCl. Those in the art will also understand that a variety of methods and agents may be used to oxidize the compound of Formula IX to obtain the compound of Formula III.

Referring now to FIG. 1, Scheme C, embodiments of methods according to the present invention wherein the compound having a ring structure that, when opened, provides a substituent having the structure of Formula I is a compound of Formula XI:

Formula XI will now be described. The compounds of Formula IX may be made, for example, by chiral epoxidation of alkenes such as alkenols, as will be understood by those skilled in the art. The preferred compound of Formula XI is 2-methyl-1,2-epoxypropanol ($R^1$ is —CH$_3$ and $R^3$ is —CH$_2$OH), which is commercially available from Acros Organics USA of Fair Lawn, N.J. The compound of Formula XI contacts the compound of Formula II under conditions sufficient to provide a compound having the structure of Formula XII:

Formula XII

The compound of Formula II is preferably added to the compound of Formula XI via a substitution reaction, as will be understood by those skilled in the art. For example, a substitution reaction similar to the one described below in Example 3 may be used. The compound of Formula XII is then oxidized, as will be understood by those skilled in the art, to convert $X^1$ to $X^2$ and, if necessary, convert $R^3$ to the carboxylic acid to provide the compound of Formula III. While the synthesis routes shown in FIG. 1, Scheme C show an oxidation step, it is to be understood that an oxidation step may not be required and/or desired. For example, an oxidation step may not be required and/or desired when $X^1$ is sulphonyl and/or $R^3$ is C(O)OH.

As illustrated in FIG. 1, the compound of Formula III may be converted to the acylanilide by treating the compound of Formula III with a compound having the structure of Formula XIII:

Formula XIII under conditions sufficient to provide a compound of Formula XIV:

Formula XIV

The amidation may be performed by various methods as will be understood by those skilled in the art. The amidation is preferably accomplished via in situ generation of the acid chloride using thionyl chloride as described above.

$R^{13}$ is preferably cyano, fluoro, chloro, bromo, iodo, or hydrogen. More preferably, $R^{13}$ is cyano, fluoro, chloro, bromo, iodo, and, most preferably, $R^{13}$ is cyano. $R^{14}$ is preferably perfluoroalkyl, perfluoroalkylthio, perfluoroalkylsulphinyl or perfluoroalkylsulphonyl each of having up to 4 carbon atoms. More preferably, $R^{14}$ is perfluoroalkyl, and, most preferably, $R^{14}$ is perfluoromethyl. Most preferably, $R^{15}$ is hydrogen. $X^2$ is preferably sulphonyl.

As described above, pure enantiomers of Casodex® (bicalutamide) and/or its derivatives may be asymmetrically synthesized by methods according to embodiments of the present invention. These enantiomers may be used to treat various diseases. For example, it is preferable to use the (R)-enantiomer of Casodex® (bicalutamide) synthesized by methods of the present invention to treat androgen-dependent diseases, such as prostate cancer. Casodex® (bicalutamide) and/or derivatives thereof synthesized by methods of the present invention may be used in various methods of treatment and pharmaceutical compositions such as, for example, those methods of treatment and pharmaceutical compositions described in U.S. Pat. No. 5,985,868 to Gray, the disclosure of which is incorporated herein by reference in its entirety.

The present invention will now be described with reference to the following examples. It should be appreciated that these examples are for the purposes of illustrating aspects of the present invention, and do not limit the scope of the invention as defined by the claims.

EXAMPLE 1

Synthesizing 4-Methyl-5-oxo-2-trihromomethyl-[1,31-dioxolan-4y1]-acetic acid

Bromal (89.1 mmol) and (S)-citramalic acid (74.2 mmol) were cooled to 0° C. in a 125 mL flask under inert atmosphere. Sulfuric acid (25 mL) was added dropwise with stirring. After 2 hrs. the contents were a yellow solution with a white precipitate. The ice bath was removed and the reaction was stirred overnight at room temperture. The dark solution was diluted with ice and extracted 4 times with ethyl acetate. The organic layer was back extracted with water and then was dried with $MgSO_4$. After filtration, the filtrate was concentrated to an oil. The product was obtained as a white solid after crystallization from toluene/hexanes. Yield 60%; mp 151° C. (sublimes); MS ($FAB^+$) 433 (M+Na); $^1$H NMR ($CDCl_3$): δ 5.77 (s, 1H), 3.06 (d, J=1.79, 2H), 1.74 (s, 3H); $^{13}$C NMR: δ 174.05, 105.55, 79.63, 43.68, 42.73, 25.38; IR: 3158, 2939, 1825, 1792, 1732; UV: $\lambda_{max}$ 208, $\lambda_{1/2\ max}$ 237. Anal. Calculated for $C_7H_7Br_3O_5$: C, 20.46; H, 1.72. Found: C, 20.89; H, 1.74.

EXAMPLE 2

Synthesizing 5-Bromomethyl-5-methyl-2-tribromomethyl-[1,3]dioxolan-4-one

The dioxolanone prepared in Example 1 and 2-mercaptopyridine N-oxide were suspended in $CBrCl_3$. The reaction was heated to reflux and a solution of DCC (dicyclohexylcarbodiamide) in $CBrCl_3$ was added slowly over the course of 30 minutes. The reaction was stirred for an additional hour. The product was purified by silica gel chromatography ($CH_2Cl_2$/hexanes (½)) and was obtained as white needles from the same solvents. Yield 65%; mp 110–113° C.; MS ($FAB^+$) no parent ion; $^1$H NMR δ 5.93 (s, 1H), 3.65 (d, J=1.4, 1H), 1.79 (s, 3H); $^{13}$C NMR δ 170.58, 105.39, 83.00, 43.51, 35.97, 23.38. IR: 2926, 1825, 1176. UV: $\lambda_{max}$ 210, $\lambda_{1/2\ max}$ 242. Anal. Calculated for $C_6H_6Br_4O_3$: C, 16.17; H, 1.36. Found: C, 16.38; H, 1.29.

EXAMPLE 3

Synthesizing 3-(4-Fluoro-phenylsulfanyl)-2-hydroxy-2-methyl-propionic acid

The protected hydroxyacid prepared in Example 2 was dissolved in a 1:1 mixture of isopropanol: 1M NaOH. After 3 hrs, the reaction mixture was a solution and no starting material was detectable by TLC (thin-layer chromatography). 4-Fluorobenzenethiol was then added and the reaction was stirred overnight. The reaction was then adjusted to pH 8 with HCl and was extracted 2 times with $CH_2Cl_2$. The aqueous layer was then adjusted to pH 1 and was extracted with $CH_2Cl_2$. The organic layer was concentrated to an oil, which crystallized on standing. The hydroxyacid was either used in the next reaction without further purification or was recrystallized from chloroform/petroleum ether. Yield 80%; mp 73–75° C.; MS ($FAB^+$) 230; $^1$H NMR: δ 7.43 (dd, J=9.0, J=5.1, 2H), 6.96 (dd, J=9.0, J=9.0, 2H), 3.40 (dd, J=13.8, J=0.9, 1H), 3.15 (dd, J=13.8, J=0.9, 1H), 1.53 (s, 3H); $^{13}$CNMR: δ 180.06, 162.37 (d, J=327.8), 133.93 (d, J=10.6), 130.30, 116.31 (J=29.2), 74.95, 46.22, 25.83; $^{19}$F NMR: 6–114.21. IR: 3065, 1719. UV: $\lambda_{max}$ 251.

EXAMPLE 4

Synthesizing N-(4-Cyano-3-trifluoromethyl-phenyl)-3-(4-fluoro-phenylsulfanyl)-2-hydroxy-2-methyl-propionamide The hydroxyacid prepared in Example 3 (8.5 mmol) and 4-amino-2-trifluoromethylbenzonitrile (11 mmol) were dissolved in dry DMA (dimethylacetamide) (15 mL) under inert atmosphere. After the solution had been cooled to −10° C., thionyl chloride (10 mmol) was added slowly. The reaction was stirred for 15 min at −10° C., and then the ice bath was removed. After stirring overnight at room temperature, the reaction was diluted with $CH_2Cl_2$ and was extracted one time with saturated $NaHCO_3$. The organic layer was dried with $MgSO_4$ and concentrated. The product was purified by silica gel chromatography (6% ethyl acetate in $CH_2Cl_2$). Yield 45%; MS (FAB$^+$) 399 (M+1); $^1$H NMR: δ 8.98 (s, 1H), 7.91 (s, 1H), 7.74 (m, 2H), 7.39 (m, 2H), 6.88 (m, 2H), 3.75 (d, J=14.1, 1H), 3.10 (d, J=14.1, 1H), 1.53 (s, 3H); $^{13}$CNMR: δ 173.10, 160.87, 141.38, 135.90, 133.97, 128.64, 121.84, 117.34, 116.57, 115.68, 104.83, 75.60, 46.07, 26.61; $^{19}$F NMR: δ−62.74, −113.22. IR: 3357, 3095, 2981, 2232, 1685.

EXAMPLE 5

Synthesizing N-(4-cyano-3-trifluoromethyl-phenyl)-3-(4-fluoro-phenylsulfonyl)-2-hydroxy-2-methyl-propionamide To a solution of the sulfide prepared in Example 4 (3.19 mmol) in $CH_2Cl_2$ (43 mL) was added mCPBA (meta-chloroperbenzoic acid) (9.57 mmol). After stirring overnight at room temperature, the reaction was diluted with ethyl acetate and extracted two times with $Na_2SO_3$ and $NaHCO_3$. The organic layer was dried with $MgSO_4$ and concentrated. After purification by silica gel chromatography, the product was obtained as white crystals from benzene/petroleum ether. Yield 94%; mp 178° C.; MS (FAB$^+$) 431 (M+1); $^1$H NMR: 59.16 (s, 1H), 8.00 (d, J=1.5, 1H), 7.88–7.93 (m, 2H), 7.79–7.80 (m, 2H), 7.14–7.20 (m, 2H), 5.02 (s, 1H), 4.00 (d, J=14.5, 1H), 3.51 (d, J=14.5, 1H), 1.61 (s, 3H); $^{13}$C NMR: δ 171.40, 166.03 ($J_{FC}$=256.7), 141.01, 135.65, 135.01, 133.88 ($J_{FC}$=32.4), 130.78 ($J_{FC}$=9.7), 121.92 ($J_{FC}$=272.0), 121.79, 117.23, 116.75 ($J_{FC}$=22.7), 115.26, 104.82, 74.44, 61.83, 27.80; $^{19}$F NMR: δ−62.71, − 101.63. IR: 3449, 3333, 3104, 2984, 2933, 2231, 1697, 1587, 1517. UV: $λ_{max}$ 214, 271. Anal. Calculated for $C_{18}H_{14}F_4N_2O_4S$: C, 50.23; H, 3.28; N, 6.51. Found: C, 50.01; H, 3.26; N, 6.23.

EXAMPLE 6

Biological Data Comparing Pure Enantiomers of Casodex® (bicalutamide) Synthesized by Methods of the Present Invention with Racemic Mixtures of Casodex® (bicalutamide)

The data for dihydrotestosterone are EC50 values. The rest of the data are IC50 values, since the assay is measuring the amount of compound it takes to reduce the testosterone response 50%.

| Compound | Experiment 1 | Experiment 2 |
|---|---|---|
| DHT (Standard) | 0.18 nM | 0.18 nM |
| OH Flut. (Standard) | 19 nM | 41 nM |
| Racemate | 900 nM | 1000 nM |
| (R) | 374 nM | 359 nM |
| (S) | 7700 nM | 11000 nM |

In the drawings and specification, there have been disclosed typical preferred embodiments of the invention and, although specific terms are employed, they are used in a generic and descriptive sense only and not for purposes of limitation, the scope of the invention being set forth in the following claims.

What is claimed is:

1. A method of asymmetrically synthesizing an enantiomer of an acylanilide or a derivative thereof comprising:
   (a) contacting a compound having a ring structure, said compound having the structure of Formula IV:

Formula IV wherein
   $R^1$ is alkyl having up to 4 carbons;
   $R^{2'}$ is alkylene having up to 6 carbon atoms;
   $R^9$ is hydrogen, or straight, branched or cyclic alkyl;
   $R^{10}$ is straight or branched alkyl, aryl, or $R^{11}X_3^4$, where $R^{11}$ is alkyl and $X^4$ is alkyl, halogen or aryl; and
   $X^3$ is a leaving group;
wherein said compound of Formula IV, when opened, provides a substituent having the structure of Formula I:

Formula I wherein
   $R^1$ is alkyl having up to 4 carbons;
   $R^2$ is alkyl having up to 6 carbon atoms; and
   $R^3$ is $CH_2OR^4$ where $R^4$ is hydrogen or benzyl, $C(O)CH_3$, or $C(O)OR^5$ where $R^5$ is hydrogen or alkyl;
with a compound having a structure of Formula II:

Formula II wherein
   $R^6$ is a direct link or alkylene having up to 6 carbon atoms;
   $R^7$ is alkyl, alkenyl, hydroxyalkyl or cycloalkyl each of up to 6 carbons; or $R^7$ is phenyl which bears one, two or three substituents independently selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl; or $R^7$ is naphthyl; or $R^7$ is a 5- or 6-membered saturated or unsaturated heterocyclic which contains one, two or three heteroatoms selected from oxygen, nitrogen and sulfur, which heterocyclic may be a single ring or may be fused to a benzo-ring, and which heterocyclic is unsubstituted or bears one or two halogen, cyano or amino, or alkyl, alkoxy, alkylthio, alkylsulphinyl or alkylsulphonyl each of up to 4 carbon atoms, or oxy or hydroxy substituents, or which if sufficiently saturated may bear one or two oxo substituents; and $X^1$ is oxygen, sulfur, sulphinyl (—SO—), sulphonyl (—$SO_2$—), imino (—NH—) or alkylimino (—$NR^8$—) where $R^8$ is alkyl having up to 6 carbon atoms;

under conditions sufficient to provide a compound having the structure of Formula III:

Formula III wherein $X^2$ is oxygen, sulfur, sulphinyl (—SO—), sulphonyl (—$SO_2$—), imino (—NH—), oxidized imino alkylimino (—$NR^8$—) where $R^8$ is alkyl having up to 6 carbon atoms, or oxidized alkylimino; and (b) treating the compound of Formula III under conditions sufficient to provide a pure enantiomer of an acylanilide or a derivative thereof.

2. The method according to claim 1, wherein step (a) comprises contacting the compound of Formula IV with the compound of Formula II under conditions sufficient to provide a compound having the structure of Formula V:

Formula V

3. The method according to claim 2 further comprising treating a starting compound of citramalic acid under conditions sufficient to provide a compound having a structure of Formula IV, wherein the citramalic acid is (S)-citramalic acid, and wherein the pure enantiomer of an acylanilide is (R)-Casodex® (bicalutamide) or a derivative thereof.

4. The method according to claim 1, wherein $X^1$ is sulfur, $R^6$ is a direct link, and $R^7$ is 4-fluorophenyl, and the compound of Formula II is 4-fluorobenzenethiol.

5. The method according to claim 1, wherein step (b) comprises:

treating the compound of Formula III with a compound having the structure of Formula XIII:

Formula XIII wherein $R^{13}$ is cyano, carbamoyl, nitro, fluoro, chloro, bromo, iodo, alkanoyl, alkylthio, alkylsulphinyl, alkylsulphonyl, perfluoroalkyl, perfluoroalkylthio, perfluoroalkylsulphinyl or perfluoroalkylsulphonyl each having up to 4 carbon atoms, or phenylthio, phenylsulphinyl or phenylsulphonyl;

$R^{14}$ is cyano, cabamoyl, nitro, fluoro, chloro, bromo or iodo, or alkanoyl, alkylthio, alkylsulphinyl, alkylsulphonyl, perfluoroalkyl, perfluoroalkylthio, perfluoroalkylsulphinyl or perfluoroalkylsulphonyl each of having up to 4 carbon atoms; or phenylthio, phenylsulphinyl or phenylsulphonyl; and $R^{15}$ is hydrogen or halogen;

under conditions sufficient to provide a compound of Formula XIV:

Formula XIV wherein $X^2$ is oxygen, sulfur, sulphinyl (—SO—), sulphonyl (—$SO_2$—), imino (—NH—), alkylimino (—$NR^8$—) where $R^8$ is alkyl having up to 6 carbon atoms, or oxidized alkylimino.

* * * * *